(12) United States Patent
Ao et al.

(10) Patent No.: US 9,234,777 B2
(45) Date of Patent: Jan. 12, 2016

(54) ULTRASONIC SIGNAL COUPLER

(71) Applicant: General Electric Company, Schenectady, NY (US)

(72) Inventors: Xiaolei Shirley Ao, Lexington, MA (US); Oleg Alexander Khrakovsky, Lynn, MA (US); Yue Ma, Burlington, MA (US)

(73) Assignee: General Electric Company, Schenectady, NY (US)

( * ) Notice: Subject to any disclaimer, the term of this patent is extended or adjusted under 35 U.S.C. 154(b) by 25 days.

(21) Appl. No.: 13/668,984

(22) Filed: Nov. 5, 2012

(65) Prior Publication Data

US 2014/0123768 A1    May 8, 2014

(51) Int. Cl.
*G01N 29/24* (2006.01)
*G01F 1/66* (2006.01)
*G01N 29/22* (2006.01)

(52) U.S. Cl.
CPC .............. *G01F 1/662* (2013.01); *G01F 1/667* (2013.01); *G01N 29/222* (2013.01); *G01N 29/223* (2013.01); *G01N 29/2468* (2013.01)

(58) Field of Classification Search
CPC ....... G01F 1/662; G01F 1/667; G01N 29/222; G01N 29/223; G01N 29/2468
USPC ............ 73/617, 644, 861.25, 861.26, 861.28, 73/861.29, 861.31, 861.23
See application file for complete search history.

(56) References Cited

U.S. PATENT DOCUMENTS

| | | | |
|---|---|---|---|
| 3,575,050 A | 4/1971 | Lynnworth | |
| 3,973,152 A | 8/1976 | Karplus | |
| 4,286,470 A | 9/1981 | Lynnworth | |
| 4,320,659 A | 3/1982 | Lynnworth et al. | |
| 4,336,719 A | 6/1982 | Lynnworth | |
| 4,373,401 A | 2/1983 | Baumoel | |
| 4,754,650 A * | 7/1988 | Smalling et al. | ........... 73/861.28 |
| 4,783,997 A | 11/1988 | Lynnworth | |
| 4,787,252 A | 11/1988 | Jacobson et al. | |
| 5,159,838 A * | 11/1992 | Lynnworth | ...................... 73/644 |
| 5,251,490 A | 10/1993 | Kronberg | |
| 5,467,321 A * | 11/1995 | Baumoel | ....................... 367/140 |
| 5,515,733 A | 5/1996 | Lynnworth | |
| 5,600,073 A | 2/1997 | Hill | |
| 5,705,753 A * | 1/1998 | Hastings et al. | ........... 73/861.28 |
| 6,047,602 A | 4/2000 | Lynnworth | |
| 6,349,599 B1 | 2/2002 | Lynnworth et al. | |
| 7,343,821 B2 | 3/2008 | Panicke et al. | |

(Continued)

FOREIGN PATENT DOCUMENTS

JP            61093914 A  *  5/1986

OTHER PUBLICATIONS

PCT Search Report and Written Opinion issued Mar. 20, 2014 in connection with corresponding PCT Patent Application No. PCT/US2013/065816.

*Primary Examiner* — Laura Martin
*Assistant Examiner* — Rose M Miller
(74) *Attorney, Agent, or Firm* — Barclay Damon, LLP

(57) ABSTRACT

An ultrasonic signal coupler includes a pipe having a first ultrasonic waveguide and a second ultrasonic waveguide penetrating the pipe so that ultrasonic transducers attached to ends of the ultrasonic waveguides communicate ultrasonic signals through the ultrasonic waveguides directly through a fluid traveling through the pipe.

19 Claims, 3 Drawing Sheets

(56) References Cited

U.S. PATENT DOCUMENTS

| | | |
|---|---|---|
| 8,033,173 B2 * | 10/2011 | Ehlert et al. .................... 73/644 |
| 8,205,507 B2 | 6/2012 | Eckert et al. |
| 2003/0055340 A1 | 3/2003 | Van Klooster |
| 2003/0097879 A1 * | 5/2003 | van Klooster .............. 73/861.18 |
| 2005/0139013 A1 * | 6/2005 | Hashimoto et al. ........ 73/861.27 |
| 2009/0016555 A1 | 1/2009 | Lynnworth |
| 2009/0314088 A1 * | 12/2009 | Djordjevic et al. ............. 73/602 |
| 2012/0266679 A1 | 10/2012 | Ao et al. |

* cited by examiner

ULTRASONIC SIGNAL COUPLER

BACKGROUND OF THE INVENTION

This invention relates generally to ultrasonic flow measurement, and more particularly to an ultrasonic waveguide assembly applied in the flow measurement.

Ultrasonic flow meters are used to determine the flow rate of a variety of fluids (e.g., liquids, gases, etc.) and combinations of different fluids flowing through pipes of different sizes and shapes. One type of an ultrasonic flow meter employs a transit time method. This technique uses one or more pairs of ultrasonic transducers attached to the exterior of the pipe wall and located upstream and downstream from each other. Each of the transducers, when energized, transmits an ultrasonic signal through the flowing fluid that is detected by the other ultrasonic transducer of the pair. The velocity of the fluid flowing in the pipe can be calculated as a function of the differential transit time of ultrasonic signals as between (1) the ultrasonic signal traveling upward against the fluid flow direction from the downstream ultrasonic transducer to the upstream ultrasonic transducer, and (2) the ultrasonic signal traveling downward with the fluid flow direction from the upstream ultrasonic transducer to the downstream ultrasonic transducer.

The pair(s) of transducers can be mounted on the pipe at different relative locations, for example, the pairs of transducers can be located on opposite sides of the pipe, i.e. diametrically opposed, such that a straight line connecting the transducers passes through the pipe axis or they can be located adjacently on the same side of the pipe. In the diametric example, the ultrasonic signal transmitted by one of the transducers in the pair of transducers is not reflected off of an interior pipe surface before it is detected by the other transducer in the pair. In the latter example of adjacent transducers, the ultrasonic signal transmitted by one of the transducers in the pair of transducers is reflected by an interior surface of the pipe before it is detected by the other transducer in the pair.

In some applications, the pipes to which the ultrasonic flow meters are attached carry fluids that cause the pipe walls to reach relatively high temperatures, or the pipes may carry fluids that cause the pipe wall to reach relatively low temperatures. Consistent exposure to extreme temperatures introduces thermal stresses that diminish the useful life of the transducer. A waveguide coupled between the ultrasonic transducer and the pipe helps to prevent the extreme temperatures from damaging the piezoelectric material. However, the signal quality can decline due to poor acoustic coupling between the waveguide and the pipe wall caused by, for example, use of manual temporary attachment methods, or by poor acoustic coupling between the launch point of the ultrasonic signals into the fluid traveling through the pipe caused by accumulation of contaminants at the launch point, or by deterioration of the piezoelectric material in the transducer caused by exposure to harsh environments such as temperature extremes.

The discussion above is merely provided for general background information and is not intended to be used as an aid in determining the scope of the claimed subject matter.

BRIEF DESCRIPTION OF THE INVENTION

An ultrasonic signal coupler is disclosed that includes first and second ultrasonic waveguides that penetrate a pipe so that ultrasonic transducers attached to ends of the ultrasonic waveguides communicate ultrasonic signals directly to a fluid traveling through the pipe. In such a configuration, the ultrasonic transducers are not in direct contact with the pipe or the fluid and so are not directly exposed to the extreme temperatures of the fluid and the pipe. One side of the ultrasonic waveguide experiences the direct temperature transfer from the pipe and fluid while the other side of the waveguide is acoustically coupled to the ultrasonic transducer. The waveguide acts as a thermal isolation buffer and helps to protect the piezoelectric material in the ultrasonic transducer from the temperature extremes of fluid traveling through the pipe. The ultrasonic waveguide is typically made from a metal and is acoustically coupled directly to the fluid by penetrating the pipe. An advantage that may be realized in the practice of some disclosed embodiments of the ultrasonic signal coupler is improved accuracy in measuring fluid flow speeds and, therefore, a volume of fluid flowing through a pipe.

In one embodiment, an ultrasonic waveguide assembly comprises a pipe having an exterior surface, an interior surface, and a pipe axis. The interior surface defines an inside diameter of the pipe which may include a fluid traveling therethrough. An ultrasonic waveguide penetrates the pipe at a first location such that the ultrasonic waveguide is in direct contact with the fluid. An ultrasonic transducer is adapted to be acoustically coupled to the ultrasonic waveguide. Another ultrasonic waveguide penetrates the pipe at another location such that it is also in direct contact with the fluid. Another ultrasonic transducer is adapted to be acoustically coupled to that ultrasonic waveguide.

In another embodiment, an ultrasonic waveguide assembly comprises a pipe having an exterior surface, an interior surface, and a pipe axis. The interior surface defines an inside diameter of the pipe which may comprise a fluid traveling therethrough. An ultrasonic waveguide penetrates the pipe at a first location such that the ultrasonic waveguide is in direct contact with the fluid. The ultrasonic waveguide comprises a length, a width, and a waveguide axis. The ultrasonic waveguide penetrates the pipe such that its axis forms an acute angle with respect to the pipe axis. The length of the waveguide is greater than its width, and an ultrasonic transducer is adapted to be acoustically coupled to the ultrasonic waveguide. Another ultrasonic waveguide penetrates the pipe at another location such that it is also in direct contact with the fluid. The other ultrasonic waveguide also comprises a length, a width, and a waveguide axis, such that its waveguide axis forms an acute angle with respect to the pipe axis. Its length is also greater than its width. Another ultrasonic transducer is adapted to be acoustically coupled to this ultrasonic waveguide, and the axes of the waveguides are collinear.

In another embodiment, an ultrasonic waveguide assembly comprises a pipe having an exterior surface, an interior surface, and a pipe axis. The interior surface defines an inside diameter of the pipe which may comprise a fluid traveling therethrough. An ultrasonic waveguide penetrates the pipe and protrudes into the fluid. The ultrasonic waveguide comprises a length, a thickness, and a waveguide axis. The ultrasonic waveguide penetrates the pipe such that its axis forms an acute angle with respect to the pipe axis. Its length is greater than its thickness, and an ultrasonic transducer is adapted to be acoustically coupled to the ultrasonic waveguide. Another ultrasonic waveguide penetrates the pipe and protrudes into the fluid. It also comprises a length, a thickness, a waveguide axis, and it penetrates the pipe such that its axis forms an acute angle with respect to the pipe axis. Its length is greater than its thickness, and another ultrasonic transducer is adapted to be acoustically coupled to it.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 2:
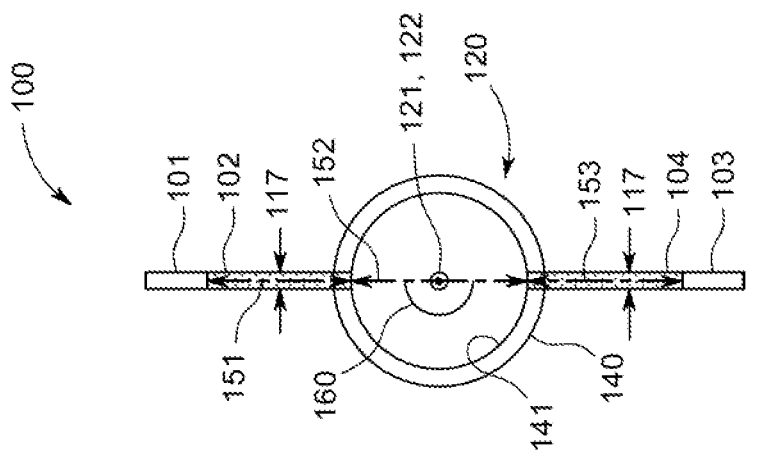
FIG. 2 is a side view of the exemplary diametric ultrasonic waveguide assembly shown in FIG. 1.
Figure 1:
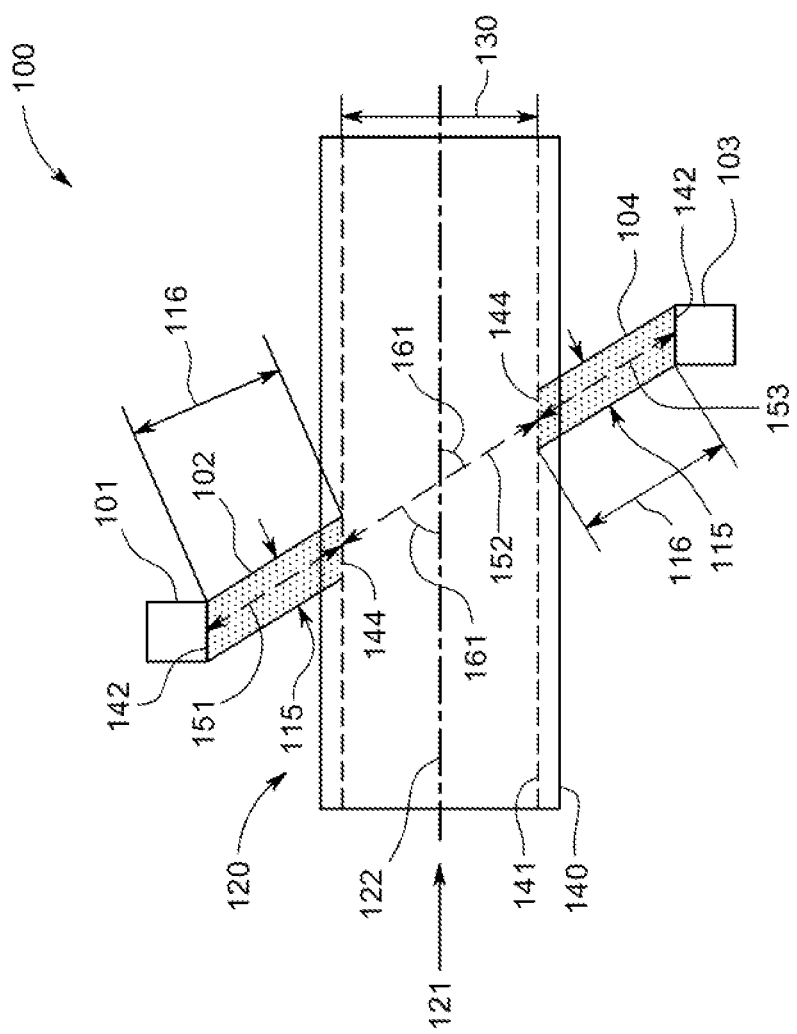
FIG. 1 is a front view of an exemplary diametric ultrasonic waveguide assembly.

FIG. 1 and FIG. 2 illustrate a front view and side view, respectively, of one embodiment of an ultrasonic waveguide assembly 100, wherein ultrasonic transducers 101, 103, are attached to ultrasonic waveguides 102, 104, respectively, which, in turn, penetrate and are attached to a pipe 120 carrying a fluid traveling in direction 121 therethrough, shown as traveling from left to right in the front view of FIG. 1, in which direction 121 is substantially parallel with an axis 122 of the pipe 120. The ultrasonic transducers 101, 103 each are capable of transmitting ultrasonic signals to each other that travel along representative ultrasonic signal path segments 151, 152, 153. Each of the ultrasonic transducers is capable of emitting ultrasonic signals and detecting ultrasonic signals. For example, when ultrasonic transducer 101 emits an ultrasonic signal it travels along representative ultrasonic signal path segment 151 through the ultrasonic waveguide 102, then is refracted along representative ultrasonic signal path segment 152 by fluid traveling through the pipe 120, then is refracted by ultrasonic waveguide 104 along representative ultrasonic signal path segment 153 through ultrasonic waveguide 104 whereby the ultrasonic signal emitted by ultrasonic transducer 101 is detected by ultrasonic transducer 103.

Similarly, when ultrasonic transducer 103 emits an ultrasonic signal it travels along representative ultrasonic signal path segment 153 through the ultrasonic waveguide 104, then is refracted along representative ultrasonic signal path segment 152 by a fluid traveling through the pipe 120, then is refracted by ultrasonic waveguide 102 along representative ultrasonic signal path segment 151 through ultrasonic waveguide 102 whereby the ultrasonic signal emitted by ultrasonic transducer 102 is detected by ultrasonic transducer 101. In one embodiment, ultrasonic waveguides 102, 104 are placed into openings through the pipe 120 and are welded in place for providing high quality acoustic coupling between the ultrasonic waveguides 102, 104 and the fluid traveling through the pipe 120. The ultrasonic waveguides 102, 104 can also be placed in pipe 120 using clamps. In either of these embodiments, the ultrasonic waveguides 102, 104 can be made of the same or different material as the pipe 120. The ultrasonic waveguides 102, 104 can be integrally formed with pipe 120 using the same material as the pipe 120 in an extrusion based fabrication process, or they can be molded into pipe 120 using the same material as the pipe in a casting fabrication process.

In the embodiment shown in FIG. 1 and FIG. 2, the parallelogram shaped ultrasonic waveguides 102, 104, each comprise a top end 142, a bottom end 144, and an ultrasonic waveguide length 116 as measured from end to end of the waveguides 102, 104 as shown in FIG. 1. Ultrasonic transducers 101, 103, are attached to top ends 142 of the waveguides 102, 104, respectively, opposite the waveguide bottom ends 144 that penetrate the pipe 120. The ultrasonic transducers 101, 103 are attached to the top ends 142 of the waveguides 102, 104, at an acute angle, an interior surface of one side of the waveguide 102, 104, respectively, forming the acute angle with the ultrasonic transducer 101, 103. Thus, the top end 142 of the ultrasonic waveguides 102, 104, respectively, and the bottom surface of each ultrasonic transducer 101, 103, respectively, are parallel to the longitudinal axis 122 of the pipe 120. The ultrasonic waveguides 102, 104, each also comprise an ultrasonic waveguide width 115 and thickness 117 that are each less than the ultrasonic waveguide length 116. The ultrasonic waveguides 102, 104 are not limited to a parallelogram shape or the same size, as depicted in FIGS. 1-2, and can also comprise a rhomboid or trapezoid shape. In one embodiment, described herein, the top end 142 and the bottom end 144 are parallel and the two side surfaces are parallel. The ultrasonic waveguides 102, 104, each also penetrate pipe 120 through exterior surface 140 of the pipe 120 and through interior surface 141 of the pipe 120 such that ultrasonic waveguides 102, 104, directly contact fluid flowing through inside diameter 130 of pipe 120. Each of the parallel side surfaces contacts the pipe 120, such that one side surface forms an interior acute angle and an exterior obtuse angle and the second side surface forms an interior obtuse angle and an exterior acute angle with the longitudinal axis of the pipe 120. Thus, each of the side surfaces of the ultrasonic waveguides 102, 104, respectively, contacts the pipe at an acute angle to the longitudinal axis of the pipe.

Figure 5:
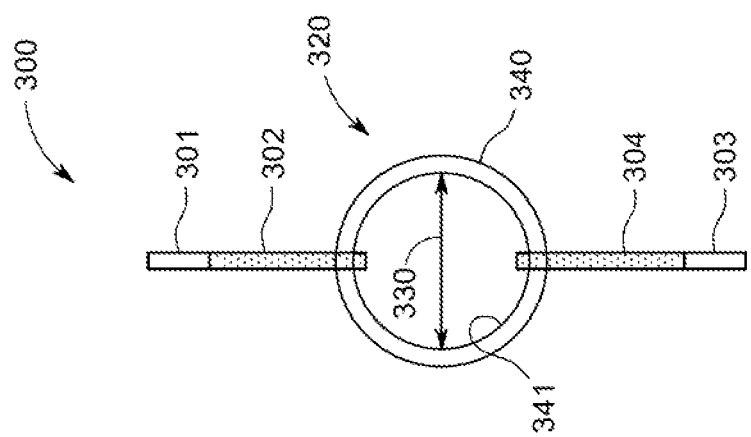
FIG. 5 is a side view of an exemplary diametric protruding ultrasonic waveguide assembly.

As illustrated in FIG. 1 and FIG. 2, the bottom end 144 of each of ultrasonic waveguides 102, 104, terminates flush with interior surface 141 of pipe 120. In one embodiment, the bottom ends 144 of the ultrasonic waveguides 102, 104 are shaped to match the curvature of the interior surface 141 of pipe 120 when the ultrasonic waveguides 102, 104 are used in a non-protruding embodiment. It should be noted that ultrasonic waveguides 102, 104, can alternatively protrude into the interior of pipe 120 (FIG. 5). This can be advantageous in some applications wherein deposits form on interior surface 141 of pipe 120 caused by fluid flowing therethrough so that the sides of ultrasonic waveguides 102, 104 that penetrate pipe 120 do not accumulate such deposits. The signal-to-noise ratio of the ultrasonic signals may also be improved by moving the end of the ultrasonic waveguides 102, 104 further into the fluid flowing through pipe 120. The ultrasonic waveguides 102, 104, each penetrate pipe 120 at an acute angle 161 formed between pipe axis 122 and the axes of ultrasonic waveguides 102, 104, which are collinear with each other and with representative ultrasonic signal path segment 152. The representative ultrasonic signal path segment 152 is used herein to also represent the axes of ultrasonic waveguides 102, 104.

In the embodiment shown in FIG. 1 and FIG. 2, the ultrasonic waveguides 102, 104, are disposed in a diametric configuration. Therefore, the ultrasonic waveguides 102, 104, are separated by 180° as measured by the angle 160 formed by a midpoint of the position where waveguide 102 penetrates the pipe 120, the central pipe axis 122, and a midpoint of the position where waveguide 104 penetrates the pipe 120. In one embodiment the ultrasonic waveguides 102, 104 are made from the same material as the pipe 120, such as carbon steel, stainless steel, or titanium. The ultrasonic transducers 101, 103 can comprise longitudinal ultrasonic transducers and shear wave ultrasonic transducers. Thus, the ultrasonic transducers 101, 103 can include ultrasonic transducers mounted on a wedge for inducing shear wave refraction between the wedge material and the ultrasonic waveguides 102, 104, respectively. In either case, representative ultrasonic signal path segments 151, 153 illustrate the ultrasonic signals emitted thereby.

A thickness of pipe 120 typically ranges from about 3 mm to 10 mm and a thickness 117 of the ultrasonic waveguides 102, 104 can vary from about 6 mm to 13 mm. Each of the ultrasonic transducers 101, 103 are electronically connected to an ultrasonic processing system (not shown) which controls the ultrasonic signals emitted by the ultrasonic transducers 101, 103 and processes the ultrasonic signals received by the ultrasonic transducers 101, 103. The time duration between ultrasonic transducer 101 emitting the ultrasonic signal and ultrasonic transducer 103 detecting the ultrasonic signal, and vice versa, is measured by the ultrasonic processing system and is referred to as a time-of-flight measurement herein.

As described above, the time-of-flight measurement for an ultrasonic signal traveling from ultrasonic transducer 101 to ultrasonic transducer 103 will be shorter than the time-of-flight measurement for an ultrasonic signal traveling from ultrasonic transducer 103 to ultrasonic transducer 101 so long as fluid is traveling through the pipe 120 in direction 121 during the time-of-flight measurement. This is because the fluid traveling through the pipe 120 is an ultrasonic sound carrying medium. Therefore, ultrasonic signals passing through the fluid in a downstream direction, e.g. from ultrasonic transducer 101 to ultrasonic transducer 103, travel faster than ultrasonic signals passing through the fluid in an upstream direction, e.g. from ultrasonic transducer 103 to ultrasonic transducer 101. The ultrasonic processing system detects this differential time-of-flight measurement to determine a speed of fluid flow through the pipe 120 in direction 121. The faster that the fluid flows through pipe 120 the greater the detected time difference. A precise correspondence is determined between the flow rate and a magnitude of the differential time-of-flight measurement and is used by the ultrasonic processing system for flow rate determination. Some of the variables that affect time-of-flight measurement include materials used for the pipe 120 and ultrasonic waveguide 102, 104, the physical dimensions of the pipe 120 and ultrasonic waveguide, 102, 104, and the type of fluid traveling through the pipe 120. In a configuration such as illustrated in FIG. 1 and FIG. 2 the transducers could be replaced without requiring a shutdown of fluid flow systems that utilize pipe 120.

Figure 4:
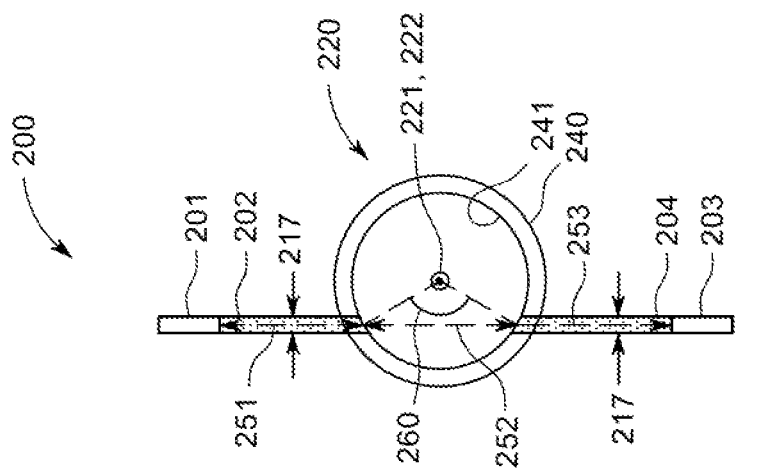
FIG. 4 is a side view of the exemplary chordal ultrasonic waveguide assembly of FIG. 3.
Figure 3:
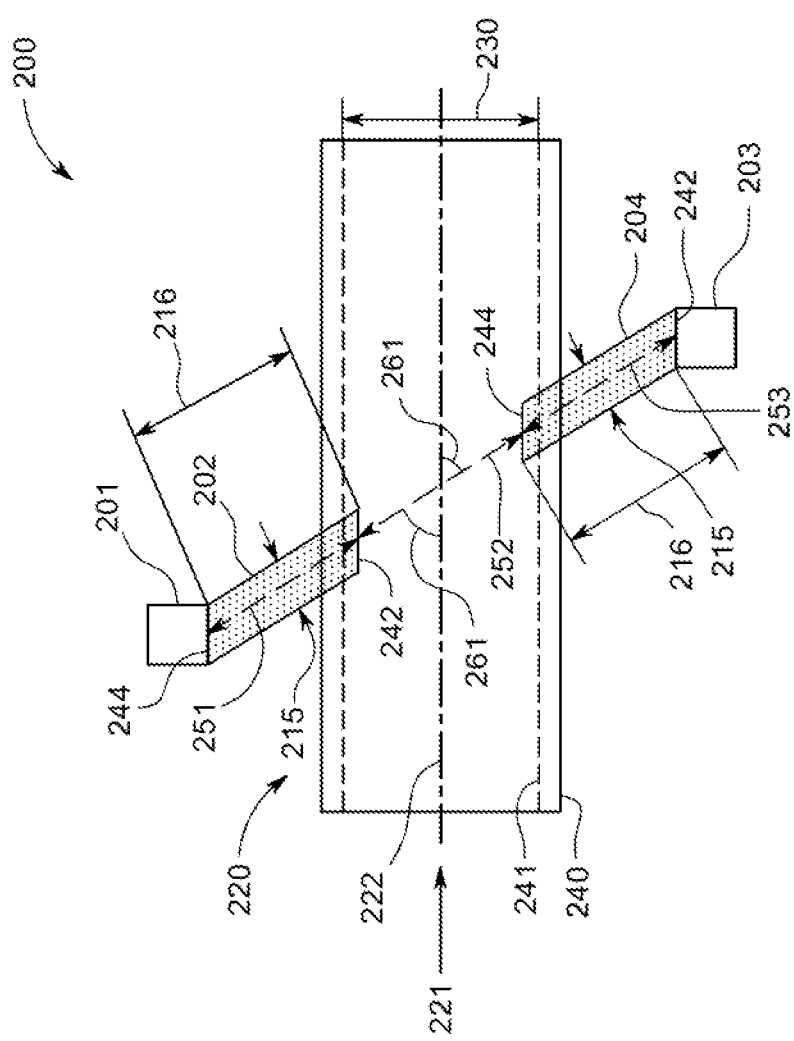
FIG. 3 is a front view of an exemplary chordal ultrasonic waveguide assembly.

FIG. 3 and FIG. 4 illustrate a front view and side view, respectively, of one embodiment of an ultrasonic waveguide assembly 200, wherein ultrasonic transducers 201, 203, are attached to ultrasonic waveguides 202, 204, respectively, which, in turn, penetrate and are attached to a pipe 220 carrying a fluid traveling in direction 221 therethrough, shown as traveling from left to right in the front view of FIG. 3, in which direction 221 is substantially parallel with an axis 222 of the pipe 220. The ultrasonic transducers 201, 203 each are capable of transmitting ultrasonic signals to each other that travel along representative ultrasonic signal path segments 251, 252, 253. Each of the ultrasonic transducers is capable of emitting ultrasonic signals and detecting ultrasonic signals. For example, when ultrasonic transducer 201 emits an ultrasonic signal, it travels along representative ultrasonic signal path segment 251 through the ultrasonic waveguide 202. The ultrasonic signal is then refracted along representative ultrasonic signal path segment 252 by fluid traveling through the pipe 220. The ultrasonic signal is then refracted by ultrasonic waveguide 204 along representative ultrasonic signal path segment 253 through ultrasonic waveguide 204 whereby the ultrasonic signal emitted by ultrasonic transducer 201 is detected by ultrasonic transducer 203.

Similarly, when ultrasonic transducer 203 emits an ultrasonic signal it travels along representative ultrasonic signal path segment 253 through the ultrasonic waveguide 204. The ultrasonic signal is then refracted along representative ultrasonic signal path segment 252 by a fluid traveling through the pipe 220. The ultrasonic signal is then refracted by ultrasonic waveguide 202 along representative ultrasonic signal path segment 251 through ultrasonic waveguide 202 whereby the ultrasonic signal emitted by ultrasonic transducer 203 is detected by ultrasonic transducer 201. In one embodiment, ultrasonic waveguides 202, 204 are placed into openings through the pipe 220 and are welded in place for providing high quality acoustic coupling between the ultrasonic waveguides 202, 204 and the fluid traveling through the pipe 220. The ultrasonic waveguides 202, 204 can also be placed in pipe 120 using clamps. In either of these embodiments, the ultrasonic waveguides 202, 204 can be made of the same or different material as the pipe 220. The ultrasonic waveguides 202, 204 can be integrally formed with pipe 220 using the same material as the pipe 220 in an extrusion based fabrication process, or they can be molded into pipe 220 using the same material as the pipe in a casting fabrication process.

In the embodiment shown in FIG. 3 and FIG. 4, the parallelogram shaped ultrasonic waveguides 202, 204, each comprise a top end 242, a bottom end 244, and an ultrasonic waveguide length 216 as measured from end to end of the waveguides 202, 204, respectively, opposite the waveguide bottom ends 244 that penetrate the pipe 220. The ultrasonic waveguides 202, 204, each also comprise an ultrasonic waveguide width 215 and thickness 217 that are each less than the ultrasonic waveguide length 216. The ultrasonic waveguides 202, 204 are not limited to a parallelogram shape or the same size, as depicted in FIGS. 3-4, and can also comprise a rhomboid or trapezoid shape and each have a different size. In one embodiment, described herein, the top end 242 and the bottom end 244 are parallel. The ultrasonic waveguides 202, 204, each also penetrate pipe 220 through exterior surface 240 and through interior surface 241 such that ultrasonic waveguides 202, 204, directly contact fluid flowing through inside diameter 230 of pipe 220.

Figure 6:
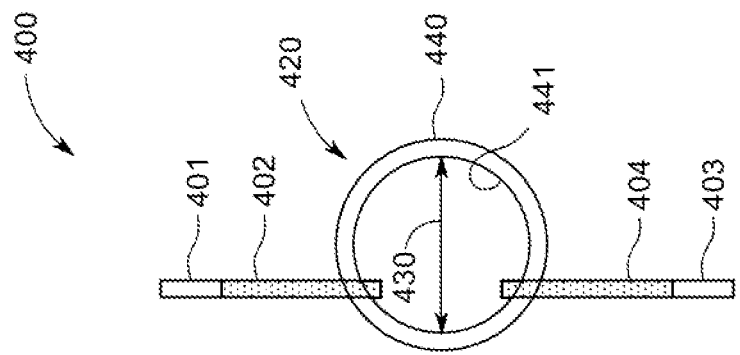
FIG. 6 is a side view of an exemplary chordal protruding ultrasonic waveguide assembly.

As illustrated in the side view of FIG. 4, a side of each of ultrasonic waveguides 202, 204, terminates flush with inside surface 241 of pipe 220. In one embodiment, the bottom ends 244 of the ultrasonic waveguides 202, 204 are shaped to match the curvature of the interior surface 241 of pipe 220 when the ultrasonic waveguides 202, 204 are used in a non-protruding embodiment. Ultrasonic waveguides 202, 204 can alternatively protrude into the interior of pipe 220 (FIG. 6). This can be advantageous in some applications wherein deposits form on inside surface 241 of pipe 220 caused by fluid flowing therethrough so that the sides of ultrasonic waveguides 202, 204, that penetrate pipe 220 do not accumulate such deposits. Signal-to-noise ratio of the ultrasonic signals may also be improved by moving the end of the ultrasonic waveguides 202, 204 further into the fluid flowing through pipe 220. The ultrasonic waveguides 202, 204, each penetrate pipe 220 at an acute angle 261 formed between pipe axis 222 and the axes of ultrasonic waveguides 202, 204, which are collinear with each other and with representative ultrasonic signal path segment 252. The representative ultrasonic signal path segment 252 is used herein to also represent the axes of ultrasonic waveguides 202, 204.

In the embodiment shown in FIG. 3 and FIG. 4, the ultrasonic waveguides 202, 204, are disposed in a chordal configuration. Therefore, the ultrasonic waveguides 202, 204, are separated by an angle 260, which is less than 180° as measured by the angle formed by the midpoint of the location where waveguide 202 penetrates the pipe 220, the central pipe axis 222, and the position where waveguide 204 penetrates the pipe 220. Thus, the difference between the diametric configuration of FIG. 1 and FIG. 2, described above, and the chordal configuration illustrated in FIG. 3 and FIG. 4 is easily distinguished. In one embodiment the ultrasonic waveguides 202, 204 are made from the same material as the pipe 220, such as carbon steel, stainless steel, or titanium. The ultrasonic transducers 201, 203 can comprise longitudinal ultrasonic transducers and shear wave ultrasonic transducers. Thus, the ultrasonic transducers 201, 203 can include ultrasonic transducers mounted on a wedge for inducing shear wave refraction between the wedge material and the ultrasonic waveguides 202, 204, respectively. In either case, representative ultrasonic signal path segments 251, 253 illustrate the ultrasonic signals emitted thereby.

A thickness of pipe 220 typically ranges from about 3 mm to 10 mm and a thickness 117 of the ultrasonic waveguides 202, 204 can vary from about 6 mm to 13 mm. Each of the ultrasonic transducers 201, 203 are electronically connected to an ultrasonic processing system (not shown) which controls the ultrasonic signals emitted by the ultrasonic transducers 201, 203 and processes the ultrasonic signals received by the ultrasonic transducers 201, 203. The time-of-flight measurement between ultrasonic transducer 201 emitting the ultrasonic signal and ultrasonic transducer 203 detecting the ultrasonic signal, and vice versa, is measured by the ultrasonic processing system.

As described above, the time-of-flight measurement for an ultrasonic signal traveling from ultrasonic transducer 201 to ultrasonic transducer 203 will be shorter than the time-of-flight measurement for an ultrasonic signal traveling from ultrasonic transducer 203 to 201 so long as fluid is traveling through the pipe 220 in direction 221 during the time-of-flight measurement. This is because the fluid traveling through the pipe 220 is an ultrasonic sound carrying medium. Therefore, ultrasonic signals passing through the fluid in a downstream direction, e.g. from ultrasonic transducer 201 to ultrasonic transducer 203, travel faster than ultrasonic signals passing through the fluid in an upstream direction, e.g. from ultrasonic transducer 203 to ultrasonic transducer 201. The ultrasonic processing system detects this differential time-of-flight measurement to determine a speed of fluid flow through the pipe 220 in direction 221. The faster that the fluid flows through pipe 220 the greater the detected time difference. A precise correspondence is determined between the flow rate and a magnitude of the differential time-of-flight measurement and is used by the ultrasonic processing system for flow rate determination. Some of the variables that affect time-of-flight measurement include materials used for the pipe 220 and ultrasonic waveguide, 202, 204, the physical dimensions of the pipe 220 and ultrasonic waveguide, 202, 204, and the type of fluid traveling through the pipe 220. In a configuration such as illustrated in FIG. 3 and FIG. 4 the transducers could be replaced without requiring a shutdown of fluid flow systems that utilize pipe 220.

FIG. 5 illustrates an alternative embodiment of an ultrasonic waveguide assembly 300, wherein ultrasonic transducers 301, 303, are attached to ultrasonic waveguides 302, 304 that penetrate exterior surface 340 and interior surface 341 of the pipe 320 and, in addition, protrude into the interior of the pipe 320 in a diametric configuration of ultrasonic waveguides 302, 304. FIG. 6 illustrates another alternative embodiment of an ultrasonic waveguide assembly 400, wherein ultrasonic transducers 401, 403, are attached to ultrasonic waveguides 402, 404 that penetrate exterior surface 440 and interior surface 441 of the pipe 420 and, in addition, protrude into the interior of the pipe 420 in a chordal configuration of ultrasonic waveguides 402, 404. The alternative embodiment of FIG. 5 operates as described above with reference to FIG. 1 and FIG. 2, and the alternative embodiment of FIG. 6 operates as described above with reference to FIG. 3 and FIG. 4. These embodiments can be advantageous in some applications, as described above, for avoiding deposits forming on the ends of ultrasonic waveguides 302, 304, 402, 404 caused by fluid flowing through pipe 320, 420, and for improving signal-to-noise ratio of the ultrasonic signals.

In view of the foregoing, embodiments of the invention provide direct communication of ultrasonic transducer signals with fluids traveling through pipes for high quality measurement of fluid flow rates. A technical effect is to accurately detect and measure physical flow speed of a fluid through pipes.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An ultrasonic waveguide assembly comprising:
 a pipe having an exterior surface and an interior surface, the interior surface defining an inside diameter of the pipe which comprises fluid traveling therethrough;
 a first ultrasonic waveguide penetrating the exterior surface of the pipe and the interior surface of the pipe at a first location such that the first ultrasonic waveguide is in direct contact with the fluid traveling therethrough, wherein the first ultrasonic waveguide comprises two end surfaces and two side surfaces arranged between the end surfaces and spaced apart along a longitudinal axis of the pipe such that the two side surfaces are substantially parallel, and each of the side surfaces of the first ultrasonic waveguide contacts the pipe at an acute angle to the longitudinal axis of the pipe;

a first ultrasonic transducer adapted to be acoustically coupled to a top end of the first ultrasonic waveguide at an acute angle such that the top end of the first ultrasonic waveguide is parallel to the longitudinal axis of the pipe;

a second ultrasonic waveguide penetrating the exterior surface of the pipe and the interior surface of the pipe at a second location such that the second ultrasonic waveguide is in direct contact with the fluid traveling therethrough, wherein the second ultrasonic waveguide comprises two end surfaces and two side surfaces arranged between the end surfaces and spaced apart along a longitudinal axis of the pipe such that the two side surfaces are substantially parallel, and each of the side surfaces of the second ultrasonic waveguide contacts the pipe at an acute angle to the longitudinal axis of the pipe; and a second ultrasonic transducer adapted to be acoustically coupled to a top end of the second ultrasonic waveguide at an acute angle such that the top end of the second ultrasonic waveguide is parallel to the longitudinal axis of the pipe.

2. The ultrasonic waveguide assembly of claim 1, wherein the first location and the second location are about 180 degrees around the pipe apart.

3. The ultrasonic waveguide assembly of claim 1, wherein the first and second ultrasonic waveguides each penetrate the pipe at an acute angle with respect to a longitudinal axis of the pipe.

4. The ultrasonic waveguide assembly of claim 1, wherein the first and second ultrasonic waveguides each comprise an axis and the axes of the first and second ultrasonic waveguide are collinear.

5. The ultrasonic waveguide assembly of claim 1, wherein the first and second ultrasonic waveguides each comprise a length and a width, and wherein each of the lengths is greater than a corresponding one of the widths.

6. The ultrasonic waveguide assembly of claim 5, wherein the first and second ultrasonic waveguides each further comprise a thickness and wherein each of the lengths is greater than a corresponding one of the thicknesses.

7. The ultrasonic waveguide assembly of claim 1, wherein at least one of the first and second ultrasonic waveguides protrude into an interior of the pipe.

8. The ultrasonic waveguide assembly of claim 1, wherein the first and second ultrasonic waveguides are each made from carbon steel, stainless steel, or a combination thereof.

9. The ultrasonic waveguide assembly of claim 1, wherein each of the first and second ultrasonic transducers emit ultrasonic signals that are detected by the other one of the first and second ultrasonic transducers.

10. The ultrasonic waveguide assembly of claim 1, wherein the first location and the second location are less than 180 degrees around the pipe apart.

11. The ultrasonic waveguide assembly of claim 1, wherein at least one of the first and second ultrasonic waveguides terminates flush with an interior surface of the pipe.

12. An ultrasonic waveguide assembly comprising:

a pipe having an exterior surface, an interior surface, and a pipe axis, the interior surface defining an inside diameter of the pipe which comprises fluid traveling therethrough in a direction substantially parallel with the pipe axis;

a first ultrasonic waveguide penetrating the exterior surface of the pipe and the interior surface of the pipe at a first location such that the first ultrasonic waveguide is in direct contact with the fluid traveling therethrough, wherein the first ultrasonic waveguide comprises a first waveguide length, a first waveguide width, and a first waveguide axis, the first ultrasonic waveguide penetrates the pipe such that the first waveguide axis forms an acute angle with respect to the pipe axis, the first waveguide length is greater than the first waveguide width, the first ultrasonic waveguide comprises two end surfaces and two side surfaces arranged between the end surfaces and spaced apart along a longitudinal axis of the pipe such that the two side surfaces are substantially parallel, and each of the side surfaces of the first ultrasonic waveguide contacts the pipe at an acute angle to the longitudinal axis of the pipe;

a first ultrasonic transducer adapted to be acoustically coupled to a top end of the first ultrasonic waveguide at an acute angle such that the top end of the first ultrasonic waveguide is parallel to the longitudinal axis of the pipe;

a second ultrasonic waveguide penetrating the exterior surface of the pipe and the interior surface of the pipe at a second location such that the second ultrasonic waveguide is in direct contact with the fluid traveling therethrough, wherein the second ultrasonic waveguide comprises a second waveguide length, a second waveguide width, and a second waveguide axis, the second ultrasonic waveguide penetrates the pipe such that the second waveguide axis forms an acute angle with respect to the pipe axis, the second waveguide length is greater than the second waveguide width, the second waveguide axis is collinear with the first waveguide axis, the second ultrasonic waveguide comprises two end surfaces and two side surfaces arranged between the end surfaces and spaced apart along a longitudinal axis of the pipe such that the two side surfaces are substantially parallel, and each of the side surfaces of the second ultrasonic waveguide contacts the pipe at an acute angle to the longitudinal axis of the pipe; and a second ultrasonic transducer adapted to be acoustically coupled to a top end of the second ultrasonic waveguide at an acute angle such that the top end of the second ultrasonic waveguide is parallel to the longitudinal axis of the pipe.

13. The ultrasonic waveguide assembly of claim 12, wherein the first location and the second location are about 180 degrees around the pipe apart.

14. The ultrasonic waveguide assembly of claim 12, wherein at least one of the first and second ultrasonic waveguides protrude into an interior of the pipe.

15. The ultrasonic waveguide assembly of claim 12, wherein at least one of the first and second ultrasonic waveguides terminates flush with an interior surface of the pipe.

16. An ultrasonic waveguide assembly comprising:

a pipe having an exterior surface, an interior surface, and a pipe axis, the interior surface defining an inside diameter of the pipe which comprises fluid traveling therethrough in a direction substantially parallel with the pipe axis;

a first ultrasonic waveguide penetrating the exterior surface of the pipe and the interior surface of the pipe, and protruding into an interior of the pipe at a first location such that the first ultrasonic waveguide is in direct contact with the fluid traveling therethrough, wherein the first ultrasonic waveguide comprises a first waveguide length, a first waveguide thickness, and a first waveguide axis, the first ultrasonic waveguide penetrates the pipe such that the first waveguide axis forms an acute angle with respect to the pipe axis, the first waveguide length is greater than the first waveguide thickness, the first ultrasonic waveguide comprises two end surfaces and two side surfaces arranged between the end surfaces and spaced apart along a longitudinal axis of the pipe such that the two side surfaces are substantially parallel, and each of the side surfaces of the first ultrasonic waveguide contacts the pipe at an acute angle to the longitudinal axis of the pipe;

a first ultrasonic transducer adapted to be acoustically coupled to a top end of the first ultrasonic waveguide at an acute angle such that the top end of the first ultrasonic waveguide is parallel to the longitudinal axis of the pipe;

a second ultrasonic waveguide penetrating the exterior surface of the pipe and the interior surface of the pipe, and protruding into an interior of the pipe at a second location such that the second ultrasonic waveguide is in direct contact with the fluid traveling therethrough, wherein the second ultrasonic waveguide comprises a second waveguide length, a second waveguide thickness, and a second waveguide axis, the second ultrasonic waveguide penetrates the pipe such that the second waveguide axis forms an acute angle with respect to the pipe axis, the second waveguide length is greater than the second waveguide thickness, the second ultrasonic waveguide comprises two end surfaces and two side surfaces arranged between the end surfaces and spaced apart along a longitudinal axis of the pipe such that the two side surfaces are substantially parallel, and each of the side surfaces of the second ultrasonic waveguide contacts the pipe at an acute angle to the longitudinal axis of the pipe; and a second ultrasonic transducer adapted to be acoustically coupled to a top end of the second ultrasonic waveguide at an acute angle such that the top end of the second ultrasonic waveguide is parallel to the longitudinal axis of the pipe.

17. The ultrasonic waveguide assembly of claim 16, wherein the first location and the second location are less than 180 degrees around the pipe apart.

18. The ultrasonic waveguide assembly of claim 16, wherein at least one of the first and second ultrasonic waveguides terminates flush with an interior surface of the pipe.

19. The ultrasonic waveguide assembly of claim 17, wherein the first waveguide axis is collinear with the second waveguide axis.

* * * * *